(12) United States Patent
Miller et al.

(10) Patent No.: US 8,840,555 B2
(45) Date of Patent: Sep. 23, 2014

(54) SYSTEM AND METHOD OF ULTRASOUND IMAGE PROCESSING

(75) Inventors: Nathan D. Miller, Middleton, WI (US); Hirohito Kobayashi, Madison, WI (US)

(73) Assignee: Echometrix, LLC, Madison, WI (US)

(*) Notice: Subject to any disclaimer, the term of this patent is extended or adjusted under 35 U.S.C. 154(b) by 187 days.

(21) Appl. No.: 13/293,499

(22) Filed: Nov. 10, 2011

(65) Prior Publication Data

US 2012/0116219 A1 May 10, 2012

Related U.S. Application Data

(60) Provisional application No. 61/412,071, filed on Nov. 10, 2010.

(51) Int. Cl.
*A61B 8/00* (2006.01)

(52) U.S. Cl.
USPC ............................ 600/438; 600/437; 600/443

(58) Field of Classification Search
CPC ........................................................ A61B 8/485
USPC ...................................................... 600/438
See application file for complete search history.

(56) References Cited

U.S. PATENT DOCUMENTS

| | | | | |
|---|---|---|---|---|
| 5,622,174 A * | 4/1997 | Yamazaki | ...................... | 600/441 |
| 5,669,387 A * | 9/1997 | Mine | ............................ | 600/455 |
| 5,673,700 A * | 10/1997 | Yamazaki et al. | ............ | 600/455 |
| 5,701,897 A * | 12/1997 | Sano | ............................ | 600/453 |
| 6,442,287 B1 * | 8/2002 | Jiang et al. | .................... | 382/128 |
| 6,558,324 B1 * | 5/2003 | Von Behren et al. | ......... | 600/440 |
| 6,757,414 B1 * | 6/2004 | Turek et al. | ................... | 382/128 |
| 6,771,803 B1 * | 8/2004 | Turek et al. | ................... | 382/131 |
| 6,785,409 B1 * | 8/2004 | Suri | ............................. | 382/128 |
| 7,257,244 B2 * | 8/2007 | Miga | ............................. | 382/128 |
| 7,421,101 B2 * | 9/2008 | Georgescu et al. | ........... | 382/128 |
| 7,466,848 B2 * | 12/2008 | Metaxas et al. | ............... | 382/128 |
| 7,664,298 B2 * | 2/2010 | Lang et al. | .................... | 382/128 |
| 7,678,051 B2 * | 3/2010 | Fan et al. | ...................... | 600/438 |
| 7,689,021 B2 * | 3/2010 | Shekhar et al. | ............... | 382/131 |

(Continued)

FOREIGN PATENT DOCUMENTS

WO 2006065615 A1 6/2006

OTHER PUBLICATIONS

Duenwald et al, "Ultrasound echo is related to stress and strain in tendon", Journal of Biomechanics 44 (2011) 424-429.*

(Continued)

*Primary Examiner* — Nicholas Evoy
(74) *Attorney, Agent, or Firm* — Ziolkowski Patent Solutions Group, SC

(57) ABSTRACT

An ultrasound system includes an ultrasound transducer adapted to obtain a dynamic series of echo signals of a subject tissue at different deformation states, and an image processor for generating and displaying ultrasound images of the tissue. The processor is configured to generate dynamic images that correspond to the dynamic series of echo signals, identify a plurality of pixels within a region of interest (ROI) of a first of the generated images, evaluate local tissue mechanical behavior by tracking the displacement, deformation, and echo intensity of the identified plurality of pixels from the first image to subsequent images based on groups of pixels that correspond to each of the identified plurality of pixels, determine tissue functionality in the subject at the tracked pixel locations, and display the tissue functionality in dynamic images that corresponds to the tracked pixel locations.

8 Claims, 7 Drawing Sheets

(56) References Cited

U.S. PATENT DOCUMENTS

| | | | |
|---|---|---|---|
| 7,693,563 B2* | 4/2010 | Suresh et al. | 600/407 |
| 7,736,315 B2* | 6/2010 | Vanderby et al. | 600/438 |
| 7,744,535 B2* | 6/2010 | Vanderby et al. | 600/438 |
| 8,282,553 B2* | 10/2012 | Vanderby et al. | 600/437 |
| 8,332,166 B2* | 12/2012 | Vanderby et al. | 702/42 |
| 8,480,582 B2* | 7/2013 | Tsujino et al. | 600/437 |
| 2003/0065260 A1* | 4/2003 | Cheng et al. | 600/427 |
| 2003/0171668 A1* | 9/2003 | Tsujino et al. | 600/407 |
| 2004/0153128 A1* | 8/2004 | Suresh et al. | 607/14 |
| 2004/0234113 A1* | 11/2004 | Miga | 382/128 |
| 2005/0027188 A1* | 2/2005 | Metaxas et al. | 600/410 |
| 2005/0074154 A1* | 4/2005 | Georgescu et al. | 382/128 |
| 2006/0025682 A1* | 2/2006 | Vanderby et al. | 600/438 |
| 2007/0073145 A1* | 3/2007 | Fan et al. | 600/437 |
| 2007/0089530 A1* | 4/2007 | Vanderby et al. | 73/801 |
| 2007/0237370 A1* | 10/2007 | Zhou et al. | 382/128 |
| 2008/0188744 A1* | 8/2008 | Fan et al. | 600/438 |
| 2009/0036779 A1* | 2/2009 | Fukuda et al. | 600/459 |
| 2009/0143676 A1* | 6/2009 | Matsumura | 600/438 |
| 2009/0216123 A1* | 8/2009 | Matsumura et al. | 600/443 |
| 2010/0027861 A1* | 2/2010 | Shekhar et al. | 382/131 |
| 2010/0036250 A1* | 2/2010 | Shin et al. | 600/443 |
| 2010/0179413 A1* | 7/2010 | Kadour et al. | 600/411 |
| 2010/0228125 A1* | 9/2010 | Vanderby et al. | 600/438 |

OTHER PUBLICATIONS

Fiorentino et al., "Activation and aponeurosis morphology affect in vivo muscle tissue strains near the muotendinous junction", Journal of Biomechanics 45 (2012) 647-652.*

Notomi et al., "Measurement of Ventricular Torsion by Two-Dimensional Ultrasound Speckle Tracking Imaging", Cardiac Imaging, vol. 45, No. 12, 2005.*

Okotie et al., "Tendon Strain Measurements With Dynamic Ultrasound Images: Evaluation of Digital Image Correlation," Journal of Biomechanical Engineering, Feb. 2012, vol. 134.*

Stefani et al., "Two-dimensional tracking and TDI are consistent methods for evaluating myocardial longitudinal peak strain in left and right ventricle basal segments in athletes," Cardiovascular Ultrasound 2007, 5:7.*

* cited by examiner

SYSTEM AND METHOD OF ULTRASOUND IMAGE PROCESSING

CROSS-REFERENCE TO RELATED APPLICATION

The present application claims priority to U.S. Provisional Application 61/412,071 filed Nov. 10, 2010, the disclosure of which is incorporated herein.

BACKGROUND OF THE INVENTION

Embodiments of the invention relate generally to ultrasound systems and methods for using ultrasound systems. More particularly, embodiments of the invention relate to a system and method for ultrasound image processing.

Conventional ultrasonic imaging provides a mapping of ultrasonic echo signals onto an image plane where the intensity of the echo, caused principally by relatively small differences in material properties between adjacent material types, is mapped to brightness of pixels on the image plane. While such images serve to distinguish rough structure within the body, they provide limited insight into the physical properties of the imaged materials. Ultrasound-based diagnostic medical imaging techniques are used to visualize muscles, tendons, and many internal organs, to capture their size, structure and any pathological lesions with real time tomographic images. Ultrasound has been used by healthcare providers to image the human body for at least 50 years and has become one of the most widely used diagnostic tools in modern medicine. The technology is relatively inexpensive and portable, especially when compared with other medical imaging modalities.

Ultrasound technologies can be used to visualize and discern various medical information from soft tissues. However, the mechanical material properties (i.e. load versus deformation) of soft tissues such as tendon and ligament are nonlinear, deformation-dependent, and can reflect the pathological state of the tissue. Finding a non-invasive way of assessing these properties is a difficult task, but ultrasound techniques and systems can be utilized.

Today, most musculoskeletal pathologies are diagnosed by observing images captured through modalities such as MRI or Ultrasound. Often, key image texture changes affecting tissue pathology are observed. Yet, this observation-based diagnosis is highly subjective and observer-dependent. Hence an economical, yet objective ultrasound assessment method or imaging technology has been sought. To satisfy this clinical demand, additional ultrasound imaging technologies have been developed.

It is well known that tissue mechanical functionality (stiffness-strain relation and all other properties that can be deduced from this relation) is a function of mechanical behavior (deformation and displacement and all other properties that can be deduced from deformation and displacement). The tissue mechanical functionality is specific to each tissue type and tissue health status. Hence, a properly and reliably evaluated tissue mechanical functionality through a wide range of mechanical behavior can be a reliable metric for diagnosis or monitor tissue health.

With the advancement of ultrasound technology, ultrasound technology allows a fast, low cost, non-invasive and reliable measurement of both tissue mechanical functionality and tissue mechanical behavior.

However, known methods of tissue assessment with ultrasound do not provide an objective measure of the status of a pathology. Instead, typically an operator (such as a medical practitioner) observes behavior of a tissue in dynamic ultrasound images and makes a subjective determination as to the status.

It would therefore be desirable to have a system and method capable of objectively determining a status of the pathology with the tissue mechanical functionalities deduced via ultrasound dynamic image (CINE image) analysis.

BRIEF DESCRIPTION OF THE INVENTION

Embodiments of the invention provide a system and method of measuring behavior of a subject and providing an objective assessment which can be used in a diagnosis.

In accordance with one aspect of the invention, an ultrasound system includes an ultrasound transducer adapted to obtain a dynamic series of echo signals of a subject tissue at different deformation states, and an image processor for generating and displaying ultrasound images of the tissue. The processor is configured to generate dynamic images that correspond to the dynamic series of echo signals, identify a plurality of pixels within a region of interest (ROI) of a first of the generated images, evaluate local tissue mechanical behavior by tracking the displacement, deformation, and echo intensity of the identified plurality of pixels from the first image to subsequent images based on groups of pixels that correspond to each of the identified plurality of pixels, determine tissue functionality in the subject at the tracked pixel locations, and display the tissue functionality in dynamic images that corresponds to the tracked pixel locations.

In accordance with another aspect of the invention, a method of determining a deformed state of a tissue in ultrasound images, the method includes selecting pixels that are within a region of interest (ROI) of a first ultrasound image of a tissue, wherein the tissue is at a first state of deformation, identifying pixels that surround the selected pixels in the first ultrasound image, evaluating a local tissue mechanical behavior by tracking the selected pixels from the first ultrasound image to subsequent locations in subsequent ultrasound images using the identified pixels that surround the selected pixels, wherein the subsequent ultrasound images correspond to different states of tissue deformation, determining functionality of the tissue at the subsequent locations of the identified pixels, and displaying the functionality at their original or subsequent locations in an image of the tissue.

In accordance with yet another aspect of the invention, a non-transitory computer readable storage medium having stored thereon a computer program comprising instructions which when executed by a computer cause the computer to obtain a dynamic series of echo signals of a subject taken using an ultrasound transducer with a tissue of the subject at different states of deformation, generate first and second images using the obtained series of echo signals, identify target pixels and their neighboring pixels in the first image, assume locations of the target pixels and their neighboring pixels in the second image, calculate values of a mathematical norm based on the target pixels and their neighboring pixels in the first image and based on their assumed location in the second image, derive actual locations of at least the target pixels in the second image based on the values of the mathematical norm, and overlay deduced functionality or mechanical behavior of the tissue that correspond to their actual locations in the original or second image.

In accordance with still another aspect of the invention, a method for monitoring tissue pathology includes generating a first tissue functionality histogram/probability density function plot based at least in part upon motion or deformation of a first pixel between a first ultrasound image at a first deformed state and a second ultrasound image at a second deformed state, calculating a first ordinal scale aspect ratio based upon the first tissue functionality histogram, generating a second tissue functionality histogram/probability density function plot based at least in part upon motion of a second pixel between a third ultrasound image at a third deformed state and a fourth ultrasound image at a fourth deformed state, calculating a second ordinal scale aspect ratio based upon the second tissue functionality histogram/probability density function plot, and generating a time series plot based on the first ordinal scale aspect ratio and the second ordinal scale aspect ratio as an indicator of a tissue pathology.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

Terms used to describe aspects of the present invention are given their ordinary and common meaning unless specifically defined herein. For the purposes of the present application, stress is the force distributed on a unit area of material, i.e., normalized force. The stress causing stretching deformation is expressed as positive stress. The stress causing contraction/compression deformation is expressed as negative stress. Strain is normalized deformation of material. Stretching deformation is expressed with positive strain. Contraction/compression deformation is expressed with negative strain. Stress-strain relation is a stress versus strain plot.

Stiffness of a material is the slope of a stress versus strain relationship. Because each different type of material has a different stiffness, the slope of the stress-strain relationship can be an important index for material identification. This slope can be a constant for the simplest materials, but when the stress versus strain relationship is linear these are called linear materials. However, some materials such as soft biological tissues are typically not necessarily linear, and as will be further discussed, their linearity may vary as a function of whether the tissue healthy or not. Such materials have a nonlinear stress-strain relationship with a stiffness (slope of relationship) that changes with increasing strain. Soft biological tissue (and rubber-like materials as well) are usually less stiff (a lower slope) at low levels of strain and stiffer (a higher slope) at higher levels of strain. Generally, the nonlinear stress-strain relation of a material is very specific to each material and considered as a signature of each material.

A "stiffness gradient" is due to the nonlinear nature of the stress-strain relation and a typical stiffness-strain relation deduced from a stress-strain relation is also a relationship (nonlinear) that changes with varying strain. The slope of this stiffness-strain relation is thus named the stiffness gradient. A set of parameters describing this curve can be considered as indices of material stiffness caused by applied strain. Generally, the stiffness gradient is also considered as a parameter that is specific to each material.

Figure 1:
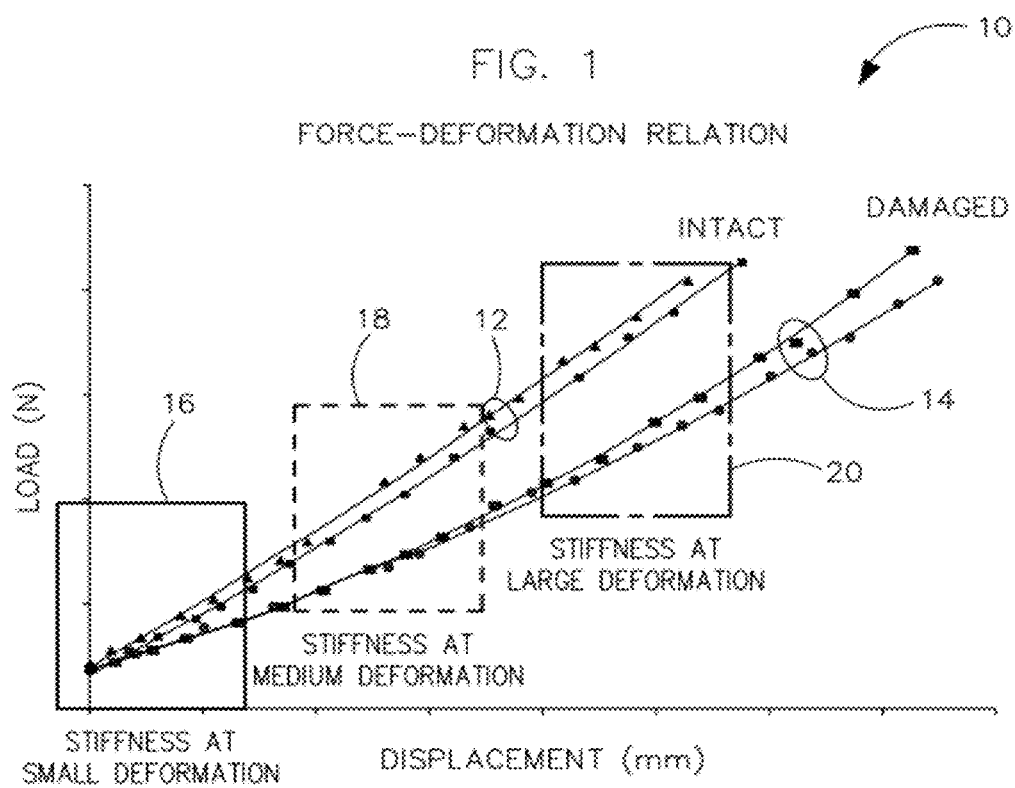
FIG. 1 is a force-deformation plot illustrating behavior of intact versus damaged tissue.
Figure 2:
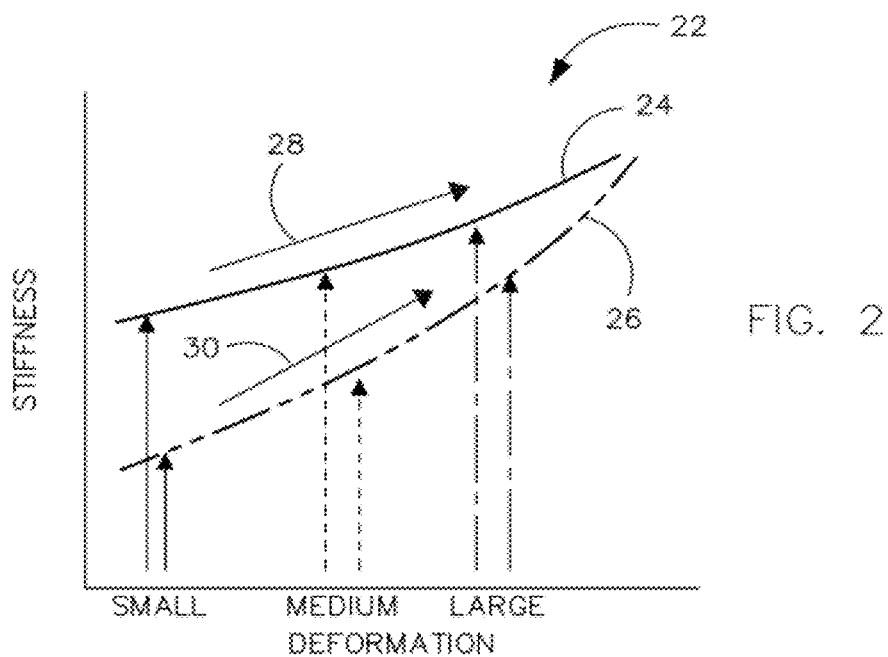
FIG. 2 is a stiffness plot as a function of material deformation.

Derivation of exemplary stiffness gradients for biological tissues is illustrated in FIGS. 1 and 2. Referring to FIG. 1, generic displacement versus load is shown for exemplary biological tissues, such as tendons, that are intact (i.e., healthy) and damaged (i.e., injured and not healed). In general a healthy biological tissue will exhibit a different stiffness than that of an injured tissue. Thus, load-displacement curve 10 includes exemplary measured data for two measurements of intact or healthy tissue 12 and for two measurements of damaged or injured tissue 14. As known in the art, stiffness of a material is generally known as the ratio of the force and deformation. As can be seen, at small deformation 16, medium deformation 18, and large deformation 20, damaged tissue 14 has a lower slope than that of injured tissue 14. In this example, the injured tissue has a lower corresponding load for a comparable displacement than does a healthy tissue. In other words, for a given load, the healthy tissue will displace less than will the damaged tissue. The general slope of measurements 12 and 14 is shown in FIG. 2 (thus, the healthy 12 and damaged 14 curves are only illustrated as single respective curves). Taking the derivative of the load curves thereby yields stiffness plot 22. Stiffness plot 22 includes healthy tissue curve 24 and injured tissue curve 26 which, as can be seen, are not linear. In this example, the healthy tissue curve 24 has a larger slope 28 for relatively smaller deformation than that 30 of injured tissue curve 26, and their slope difference decreases with increasing deformation. It is the slope of these curves that can be taken advantage of, according to the invention. Thus, as known in the art, different magnitude of stiffness is discernible in the echoes of ultrasound measurements.

Acoustic impedance is defined as the mathematical product of density and acoustic velocity, or square root of the product between density and stiffness. Ultrasound echo reflection is caused at the interface between two materials with different acoustic impedance. In the case of a biological tissue, the density of most tissues is a similar value (close to the density of water), the impedance difference of tissues are directly linked to stiffness differences. However, even the stiffness differences of different tissue types at a not-deformed state (not-loaded state) are minute, hence echo reflection is small that results in an unclear ultrasound image.

The acoustoelastic (AE) effect in elastic media occurs when acoustic waves propagate through deformed elastic media, acoustic characteristics (acoustic impedance, wave velocity, reflected echo magnitude) depend on material properties and magnitude of applied deformation. This phenomenon is called acoustoelasticity and the theory of acoustoelasticity provides a set of equations to analyze. Thus, when a biological tissue such as a tendon is flexed, the flexing causes a change in the amount of tension, which can be observed using ultrasonic images, according to the invention. Thus, in principle and as known in the art, deforming a tendon while receiving echoes from an ultrasound imaging apparatus can yield ultrasound images that highlight changes in the stiffness of the material that can be indicative of a level of injury in the tendon by processing acquired ultrasound dynamic image (also widely known as CINE image). Thus, such measurements can be employed to monitor a tissue as it heals, and ultrasound images may be taken over a period of weeks or months, as examples, to provide a means of observing the status of the tissue.

However, the act of flexing the tendon causes motion of the tendon to occur. Thus, in order to view an injured tendon the tendon is, paradoxically, caused to move (by the patient flexing a toe, for instance), which prevents a reference frame from being maintained from one image to the next during a dynamic (cine) ultrasound imaging session. As such, according to the invention, a region-of-interest (ROI) is established which can be maintained from image to image in a dynamic session, enabling both tissue functionality such as stiffness and tissue mechanical behavior such as tissue strain in an injured tendon, for instance, to be monitored despite it being moved in order to cause deformation and displacement of the tendon.

According to the invention, the ROI for analysis can be selected by a user on an image frame of dynamic ultrasound images. In one embodiment, a fiber-of-interest (FOI) for analysis can be selected by a user on an image frame of dynamic ultrasound images. According to one embodiment, the ROI and FOI can be selected on a first image (image of tissue resting state without deformation) of the dynamic ultrasound images and in another embodiment the ROI or FOI are selected on other than the first image frame of ultrasound dynamic images.

As implied, deformation-dependent stiffness is directly related to the echo intensity. Hence the deformation-dependent stiffness is calculated by assuming the echo intensity at any region to be "stiffness" that is modeled as the linear combination of finite numbers of constants and the same strain evaluated at the pixel. Deformation-dependent stress is a deformation-dependent function that is evaluated by integrating "deformation-dependent stiffness."

Pattern recognition aims to classify data based either on a priori knowledge or on statistical information extracted from patterns. The patterns to be classified are usually groups of measurements or observations, defining points in an appropriate multidimensional space. The method and apparatus described herein can be directly implemented onto ultrasound hardware system for on site processing or delivered to any computer system as image post-processing software.

Figure 3:
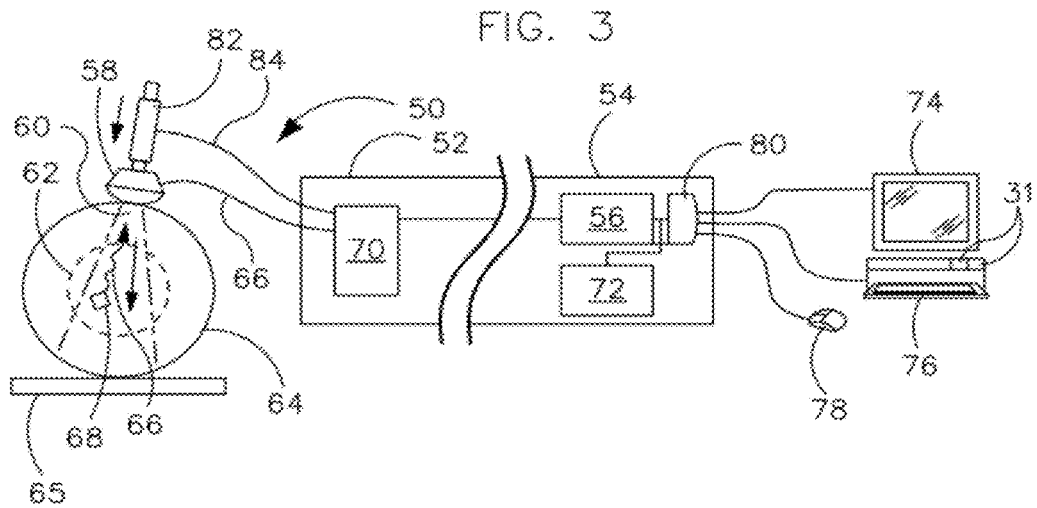
FIG. 3 is a schematic block diagram of an ultrasound scanner suitable for use with the present invention.

Referring to FIG. 3, an acoustoelastographic imaging system 50 suitable for use with the present invention may employ an ultrasonic imaging machine 52 alone or in combination with an external computer 54. According to one embodiment, computer 54 includes more than one core or CPU 31 for performing calculations, enabling quicker analysis of a region-of-interest, as will be further described. Generally, the ultrasonic imaging machine 52 provides the necessary hardware and/or software to collect and process ultrasonic echo signals by a processor 56 held within the ultrasonic imaging machine 52 or in the external computer 54.

An ultrasonic transducer 58 associated with the ultrasonic imaging machine 52 may transmit an ultrasonic beam 60 toward a region of interest 62 within the patient 64 on a table 65 to produce echo signals 66 that may be received by the ultrasonic transducer 58 and converted to an electrical echo signals 66. For the construction of an image, multiple rays within ultrasonic beam 60 and echo signals 66 will be acquired through different voxels 68 in the patient so as to obtain an "echo set" of echo signals 66 from a plurality of voxels 68 within the region of interest 62.

The electrical echo signals 66 may be received by interface circuitry 70 of the ultrasonic imaging machine 52, the interface circuitry 70 providing amplification, digitization, and other signal processing as is understood in the art. The digitized echo signals may then be transmitted to a memory 72 for storage and subsequent processing by the processor 56 as will be described. The processed echo signals 66 may be used to construct an image displayed on graphical display 74. Input commands from an operator may be received via a keyboard 76 or cursor control device 78, such as a mouse, attached to the processor 56 via an interface 80 as is well understood in the art. A position sensor 82 may be attached to the ultrasonic transducer 58 to indicate orientation of the ultrasonic transducer 58 through an electrical position signal 84 also provided to the interface circuitry 70.

At least one embodiment of the method includes an algorithm that evaluates material properties of user selected ROI and/or FOI of deforming medium by analyzing captured ultrasound dynamic images. Additionally, as will be described, data input/output is a feature that manages image upload and recording the deduced composite data image. The ROI analysis includes ROI selection, tracking, deformation evaluation, ROI echo intensity monitor and material property evaluation will be achieved in this feature. The deduced ROI data can then be visualized. In another embodiment, FOI tracking is provided. FOI selection, tracking and deformation evaluation will be achieved in a similar methodology as ROI tracking, with the exception that FOI tracking is linear. The deduced FOI data will be also display in this feature.

Figure 4:
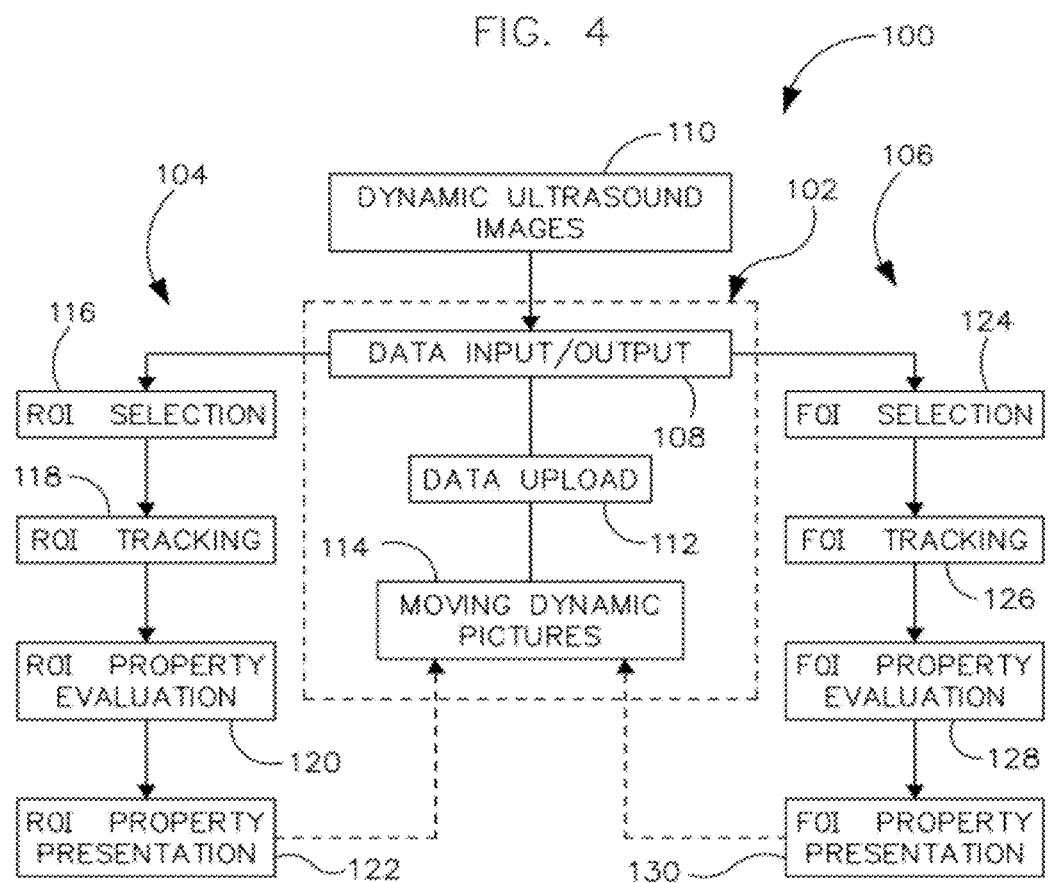
FIG. 4 is a block diagram illustrating implementation of region-of-interest (ROI) and fiber-of-interest (FOI) tracking, according to embodiments of the invention.

Referring now to FIG. 4, the illustrated method 100 consists of three key parts: data I/O 102, ROI analysis 104 and FOI analysis 106. The data I/O elements 108 of method 100 include ultrasound dynamic images 110 widely known as CINE images of the deforming target material has to be properly captured by a user with an ultrasound device such as that described with respect to FIG. 3. This method can analyze CINE images formatted with most image format including DICOM format that is widely accepted as a standard medical image saving format. Properly captured images can be uploaded 112 into a data key pad for single image analysis or multiple images analysis for data compare. Both uploaded original images and analyzed images can be transferred to movie re-player and recorder 114 for viewing and recording moving dynamic pictures. When the analyzed the images are viewed at 114, multiple deduced data can be overlaid onto an original image and presented as a composite image using either ROI tracking 104 or FOI tracking 106. The newly created composite data image can be save as any image format to be viewed by other software. Saved composite data images can be uploaded into data I/O block 108 for re-analysis on a different ROI/FOI. Uploaded images can be transferred to ROI analysis block for analysis. To achieve swift and proper AE analysis, a proper ROI is selected by a user with ROI selection function 116.

ROI selection can be achieved by a mouse click action on multiple pixels (including more than three pixels to properly define a region in an image). Once the ROI is selected and defined by the user 116, ROI inner pixels to be analyzed will be automatically defined by software. The number and location of ROI inner pixels will be automatically determined based on a default or user selected pixel spacing (density) of inner pixels. The user can select multiple ROIs for simultaneous analysis and comparison. According to the invention and as will be described, a small neighbor pixels surrounding the defined pixel will be automatically defined by an analysis algorithm. The shape of and size of neighbor region can be set default or selected by user.

Once the ROIs are selected by a user, the proposed method and system can automatically initiate ROI tracking feature 118. ROI tracking will be described further with respect to FIGS. 5 and 6. In the disclosed process, three key parameters, pixel displacement, pixel echo intensity and deformation of neighbor region surrounding each defined pixels (ROI border/inner pixels) are simultaneously evaluated and monitored. The pixel displacement monitor and evaluation of neighbor region deformation are simultaneously achieved with the tracking algorithm described below.

Figure 5:
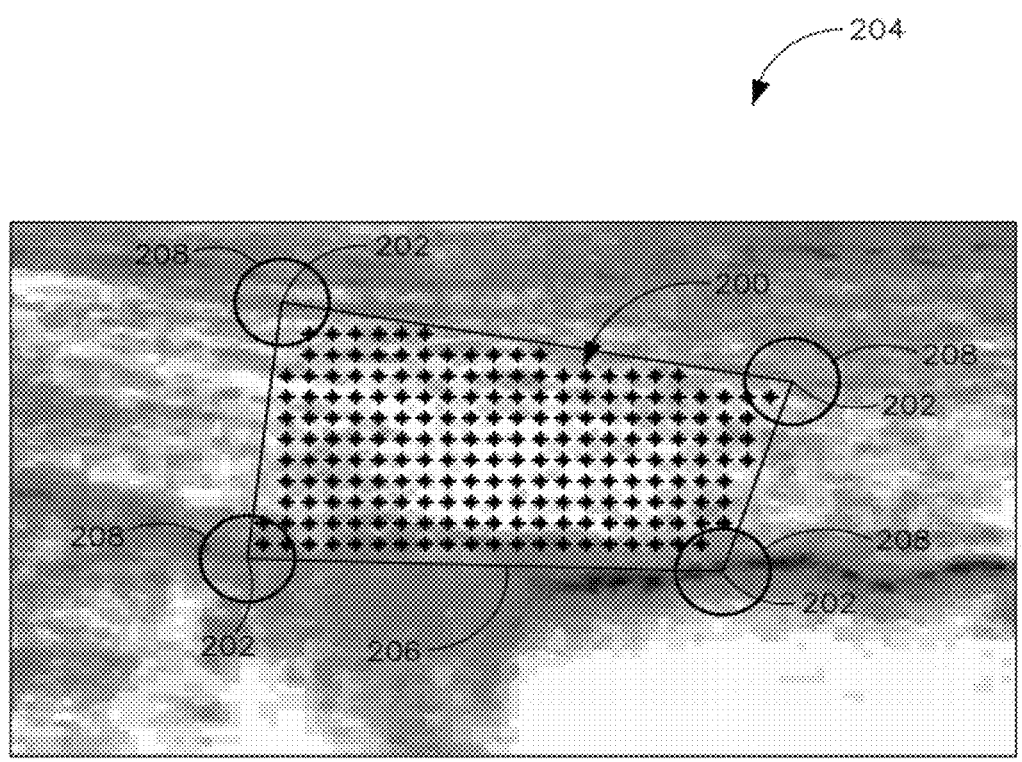
FIG. 5 illustrates an ROI of a tissue showing boundary pixels and their surrounding pixels used for motion and deformation determination, according to an embodiment of the invention.

Referring now to FIG. 5, ROI 200 is defined by, in this illustration, four corner pixels 202. ROI 200 in this embodiment is of a portion of a tendon 204. It is contemplated that, although ROI 200 is illustrated having four pixels 202 that form boundary 206, ROI 200 may be formed having three or more pixels 202 which form an area or ROI 200 therebetween.

According to the invention, ROI tracking 118 of method 100 includes tracking motion of the ROI by using pixels from the dynamic ultrasound images that surround 208 pixels 202. Thus, referring to FIG. 6, ROI tracking 300 starts 302 and pixels are identified 304 to track motion of the ROI. Such pixels may include but are not limited to pixels 202 of portion of a tendon 204 in FIG. 5. Once pixels for determining displacement of the ROI are determined at step 304, pixels surrounding the identified pixels are identified at step 306.

Pixel displacement and pixel neighbor-region deformation may be calculated by optimizing properly defined mathematical norm, according to the invention. Two example mathematical norms are presented herein. In each of these two mathematical norms, displacement of a pixel from one dynamic image to the next is calculated by assuming a displacement and deformation of an element 308, calculating the value of the norm 310, and comparing it to a threshold 312. If the value of the norm is not within a predetermined threshold 314, then the assumed displacement and deformation is perturbed or otherwise altered 316, and the norm is recalculated at step 310. The process iteratively repeats until, when the value of the norm is within the given threshold 318, then the process ends 320. The process of pixel displacement and neighbor-region deformation calculation just described can be done on a number of pixels within the ROI. Thus, dynamic images obtained by, for instance, flexing a tendon, can be evaluated in order to track the movement or displacement of pixels that define the ROI and pixels within the ROI from image to image.

Figure 7:
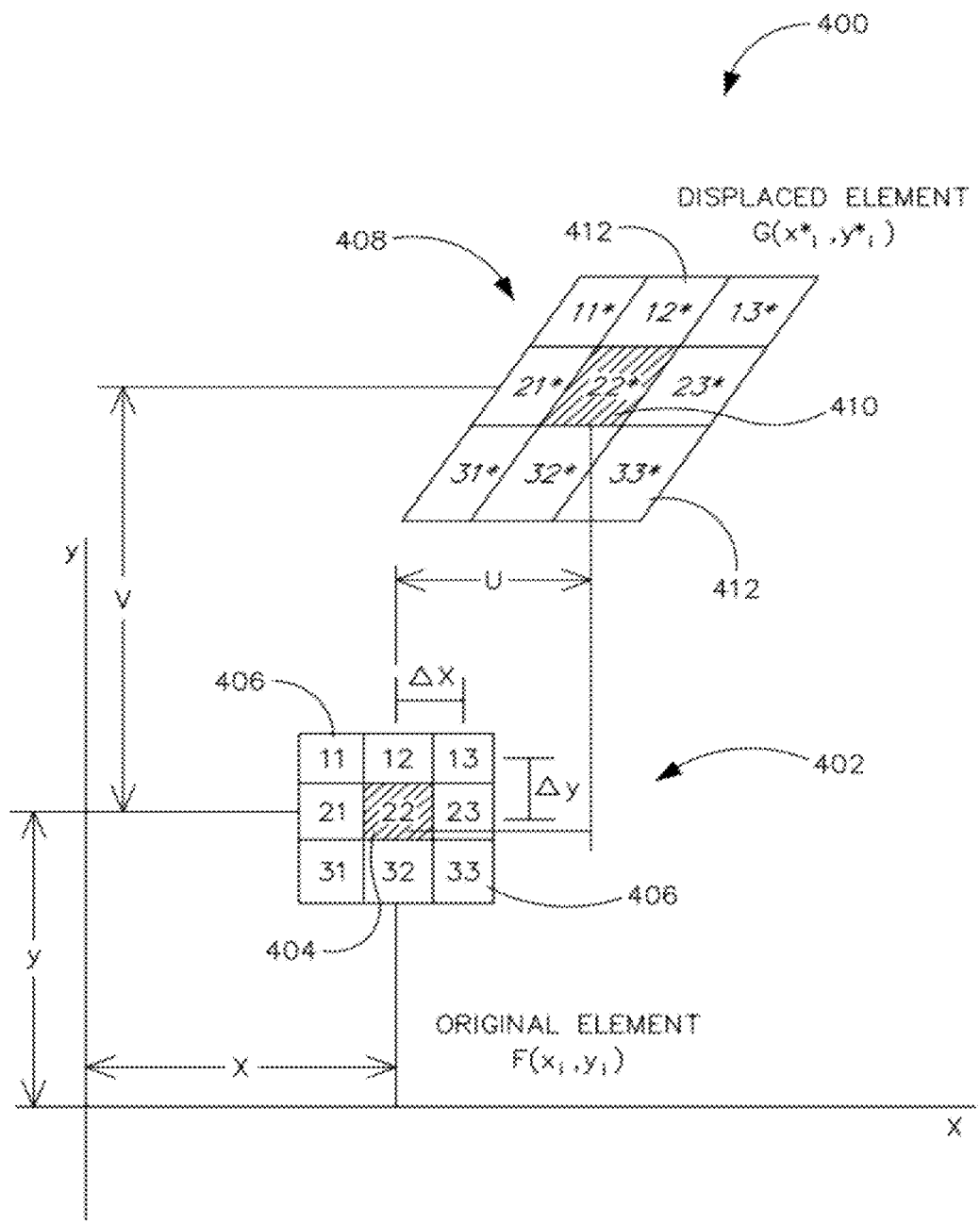
FIG. 7 is a graphical illustration of an original pixel and its surrounding pixels, and the same pixel in a different location and in a distorted state.

As stated, pixel displacement may be calculated with any one of many mathematical norms. Two example norms are described here after. Referring to FIG. 7, an X-Y plot 400 includes an original element F 402 having pixel "22" 404 at its center. Pixel "22" 404 corresponds to a selected pixel to determine its motion from image to image, such as one of pixels 202 of FIG. 5. Further, as stated with respect to FIG. 5, surrounding pixels 208 may include a radius of pixels that may include 10, 15, or more pixels in radius from pixel "22" 404. For simplicity of illustration purposes, however, only 1 pixel surrounding pixel "22" 404 is illustrated. Such are labeled in FIG. 7 as surrounding pixels 406 (elements 11, 12, 13, 21, 23, 31, 32, and 33). X-Y plot 400 also illustrates deformed and displaced element G 408 having center pixel "22*" 410 with surrounding pixels 412 (elements 11*, 12*, 13*, 21*, 23*, 31*, 32*, and 33*).

By example, assume a original pixel (pixel 22 404) is displaced u and v to new location 22* 410. Along with pixel movement, the original square shaped surround neighbor of element F 402 has deformed and translated to be G(x*,y*) 408. It is also assumed that the magnitude of both displacement and deformation take place are relatively small and can be assumed to be bounded by a small search boundary. In this circumstance, the coordinate relation between each pixel in original and deformed neighbor region for general three dimensional case be related by the following relation:

$$\vec{x}^* = \vec{x} + \vec{u} + (\nabla_x \vec{u}) \Delta \vec{x}; \qquad \text{Eqn. 0.}$$

Here $\vec{x}$, and $\Delta\vec{x}$, represent known coordinates vector of center pixel and known relative distances vector of other pixels from center pixel in the original neighbor region. The unknown displacements vectors of center pixel are represented by $\vec{u}$. However, to make the discussion simple, the two dimensional case will be used here after. In the two dimensional case the coordinate relation between each pixel in original and deformed neighbor region can be related by $$x^* = x + u + \frac{\partial u}{\partial x}\Delta x + \frac{\partial u}{\partial y}\Delta y; \text{ and} \qquad \text{Eqn. 1}$$

$$y^* = y + v + \frac{\partial v}{\partial x}\Delta x + \frac{\partial v}{\partial y}\Delta y. \qquad \text{Eqn. 2}$$

Here x, y, Δx, and Δy represent known x, y coordinates of center pixel 404 and known relative distances of other pixels from center pixel 404 in the original neighbor region 402. Unknown displacements of center pixel 404 are represented by u and v. Similarly, the unknown deformation and rotation of neighbor-region (element) are represented by the differentials $$\frac{\partial u}{\partial x}, \frac{\partial u}{\partial y}, \frac{\partial v}{\partial x}, \text{ and } \frac{\partial v}{\partial y}.$$

Mathematically defined norms for assessing the deformation of center pixel 404 include evaluation of the cross-correlation coefficient $r_{ij}$:

$$r_{ij}\left(u, v, \frac{\partial u}{\partial x}, \frac{\partial u}{\partial y}, \frac{\partial v}{\partial x}, \frac{\partial v}{\partial y}\right) = 1 - \frac{\sum_i \sum_j [F(x_i, y_j) - \overline{F}][G(x_i^*, y_j^*) - \overline{G}]}{\sqrt{\sum_i \sum_j [F(x_i, y_j) - \overline{F}]^2 \sum_i \sum_j [G(x_i^*, y_j^*) - \overline{G}]^2}}. \qquad \text{Eqn. 3}$$

or a norm of pixel intensity difference:

$$s(i,j) = \Sigma_i \Sigma_j [F(x_i, y_j) - G(x^*_i, y^*_j)]^2; \qquad \text{Eqn. 4.}$$

Here $F(x_i, y_j)$ is the gray-scale value at a point $(x_i, y_j)$ in the original image and $G(x_i^*, y_j^*)$ is the gray-scale value at a point $(x_i^*, y_j^*)$ in the deformed image. The mean values of the sub-image F and G are denoted by $\overline{F}$ and $\overline{G}$.

Figure 6:
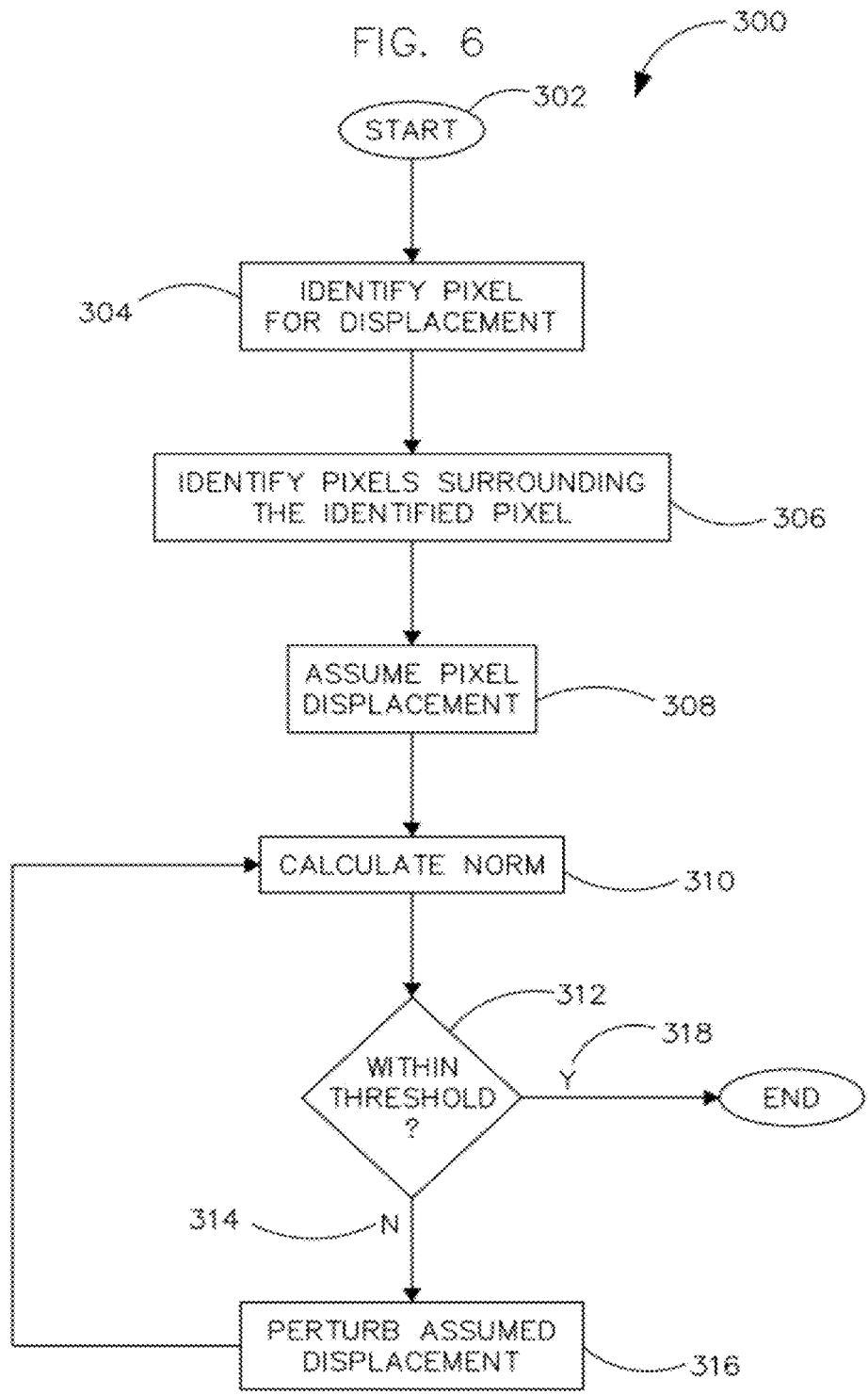
FIG. 6 is an algorithm for pixel tracking according to an embodiment of the invention.

With these mathematical relations, the step by step process for tracking center pixel by finding best match of neighbor-region can be described as follows, as described also with respect to FIG. 6:

Step 1: Assume initial displacement u, v and deformation du/dx, du/dy, dv/dx and, dv/dy and estimate new pixel coordinate x*, y* and neighbor region G(x* and y*) by equations 1 and 2.

Step 2: Evaluate mathematically defined norms (either Eqn. 3 or 4).

Step 3: Check the magnitude of the evaluated norm. If the value is below a defined threshold and/or change in u, v and deformation du/dx, du/dy, dv/dx and, dv/dy falls below a defined threshold, the new location of the neighbor region is considered found and terminate tracking.

Step 4: If the evaluated norm is relatively large, then perturb displacement u, v and deformation du/dx, du/dy, dv/dx and, dv/dy slightly and repeat process step 1 through 3 until properly small value of norm is achieved.

The disclosed process can be executed with any existing nonlinear optimization mathematical theory.

Upon the completion of the evaluation of local tissue mechanical behavior that includes pixel displacement and tracking, neighbor-region deformation evaluation and echo intensity change monitoring, this algorithm will evaluate the tissue functionality with deduced tissue mechanical behavior information. Here, the normalized material stiffness and deformation dependent normalized stiffness (stiffness gradient) are deduced from recoded pixel echo intensity and material deformation.

Since the deduced pixel displacement and pixel neighbor-region deformation are evaluated numerical value of the displacement and deformations of all pixels within ROI can be transferred onto subsequent images. Thus, returning to FIG. 4, after the above description related to ROI tracking (that includes mechanical behavior such as tissue movement and deformation), at step 120 tissue functionality or property evaluation is performed, and ROI property presentation occurs at step 122 where ROI locations and deformations are overlaid with tissue functionality such as a stiffness-strain relationship.

Referring still to FIG. 4, in a FOI assessment a practitioner selects typically two points in one of a series of dynamic images at step 124. The movement of two points are tracked at step 126 in much the same fashion as described above with respect to FIGS. 5-7. At step 128 a property of the tissue is evaluated. However, because only two points were selected, the property that is being assessed is limited to relative motion of the two points. In such fashion, a practitioner can determine, based on the evaluation, whether the tissue is undergoing deformation in the dynamic images and at the selected location. The property is presented at step 130 to the practitioner. Thus, this method also evaluates the regional material stiffness-strain for any pixel neighbor region defined at each pixel in ROI as part of ROI material property evaluation feature. Echo intensity is directly related to the stiffness. Hence the concept of the deformation-dependent stiffness is developed by assuming the echo intensity at any region to be indicative of stiffness-strain that is modeled as the linear combination of finite numbers of constants and same numbers of strain evaluated at the pixel.

This algorithm models the deformation-dependent stiffness in any sub-region in an ROI at arbitral image frame number, say N frame, as a linear combination of m numbers (picked by user) of unknown constant $a_i$ and m numbers of strains that are evaluated at the same point/region at N numbers of image frames that included current image frame (m, m−1, m−2, , , N−m+1).

$$C_N(\epsilon_N) = a_1\epsilon_N + a_2\epsilon_{N-1} + \ldots + a_m\epsilon_{N+m-1}$$

Unknown constants $a_i$ can be deduced by solving m numbers of linear equations with measured N sets of stiffness $C_N(\epsilon_N)$ and strains evaluated at the same neighbor sub-region. Deduce unknown constant $a_i$ can be feedback into above relation to describe deformation dependent material stiffness.

Finally, this algorithm can evaluate deformation-dependent normalized stress for any sub-regions by integrating deformation-dependent stiffness deduced in previous step.

Once the tissue functionality and mechanical behavior are evaluated in ROI property evaluation feature, all data are passed to an ROI presentation feature for qualitative and quantitative data presentation.

First, the deduced numerical value of the tissue functionality and mechanical behavior of all pixels within ROI can be translated into a color scheme and a color image and be produced. In addition, the same deduced numerical values of all pixels within ROI can be used to evaluate the probability density function and/or histogram and presented as a plot.

The algorithm described in this document can be directly implemented onto ultrasound hardware system for on site processing or delivered to any computer system as image post-processing software. The overview architecture of this algorithm is presented in FIG. 1.

As Numerical Data Output, all of the deduced the data can be saved with a simple viewable format such as ASCII format. ASCII format data can be easily accessed with any existing software that is available on market.

According to at least one embodiment, a fully automated tracking and ultrasound analysis is a solution for practical daily swift clinical use. To achieve that goal, currently used manual ROI selection may be replaced by an automated or systematic ROI selection. Thus, a more automated ROI selection may be achieved by one of following methods.

Method 1: Implementation of automated tendon/ligament identifier: The image texture of tendon/ligament is different from other type of tissues, such as fat, muscle and skin, hence automated tissue "differentiation", also known as "segmentation", is possible by implementing an existing digital image processing/machine vision algorithm.

Method 2: Tracking of all pixels in view space: Treating whole image as ROI and track all key pixels. Tracking all pixels can be time consuming. However, by splitting the tracking procedure into multiple cores, such as cores 31 of computer 30 of FIG. 3. Hence tracking all pixels can be accomplished.

Alternatively, the ROI tracking can be performed by utilizing an optical flow methodology. The direct output of the optical flow method is the velocity (speed in x and y direction) of a target pixel. There are two additional steps that are used to evaluate the deformation (stretch=Post motion length between two pixels—pre-motion length of two pixels) necessary for evaluation. First, the "time" factor has to be multiplied to the deduced velocity to find out the displacement of the pixel. Second, the deformation can be evaluated from pixel displacement.

In yet another alternative example, the ROI tracking can be performed utilizing a region-matching, or box matching, methodology. This method contains some similarities with the first ROI tracking methodology described above. First, a small sub-region is created around a target pixel to be tracked. The best matching sub-region through matching texture with optimization is then found.

In another embodiment, a method for monitoring tissue pathology is provided. In the deduced tissue functionality color map, each pixel contains tissue functionality data. A tissue functionality histogram/probability density function plot generated from the deduced tissue functionality. The plot can be plotted with the Frequency (frequency of pixels) on the y-axis and the deduced tissue functionality on the x-axis. The plot is then normalized to reduce the possible bias caused by differences in the region of interest. One method of normalization takes all frequency (frequency of pixels) normalized by the maximum frequency value of the deduced from other ultrasound data obtained for a particular subject from a particular data set. The aspect ratio for a particular normalized histogram is calculated. The height of the histogram (normalized-frequency) is divided by the width of the histogram (range of tissue functionality and mechanical behavior distribution) to calculate the aspect ratio. The aspect ratio is converted and utilized as an ordinal scale to differentiate tissue pathology differences over time. To assist with this differentiation, a time series plot is generated for the normalized aspect ratios obtained for a particular subject at different times. The time series plot can graphically provide data for monitoring tissue pathology changes. Based upon the time series plot certain information about the monitored tissue can be deduced.

Figure 8:
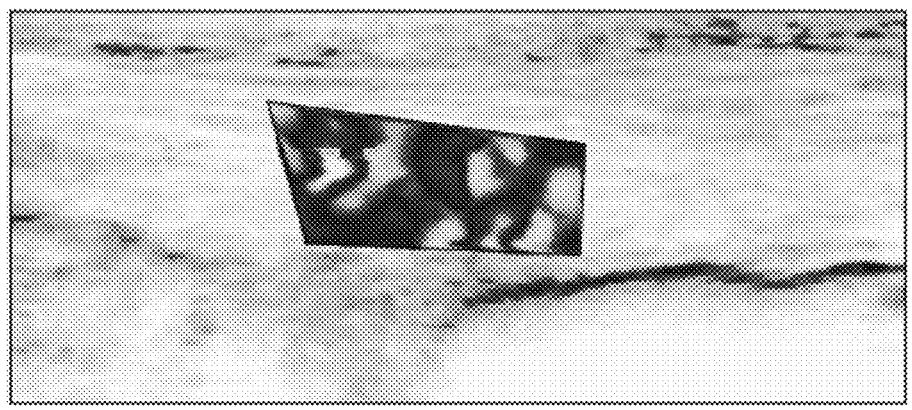
FIG. 8 is an illustration of a strain field color map ROI of a tissue obtained according to an embodiment of the invention.
Figure 9:
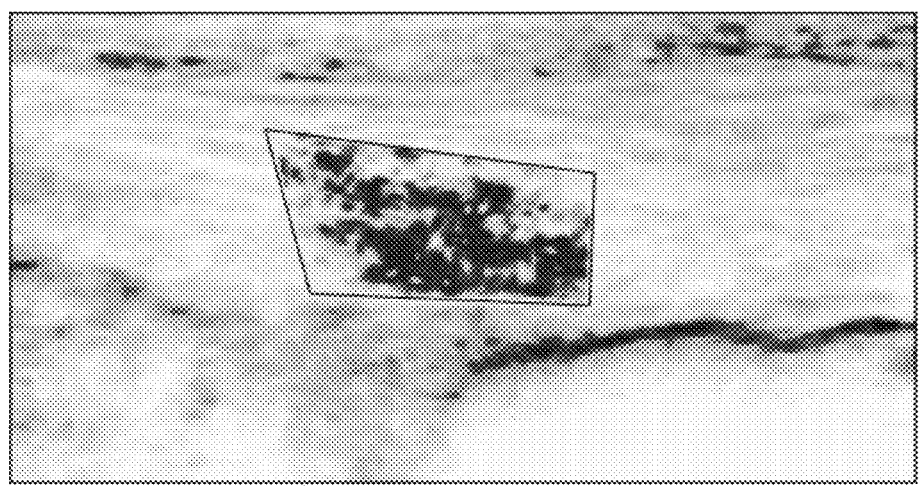
FIG. 9 is an illustration of stiffness-gradient fields (color map) overlaid onto the ROI according to an embodiment of the invention.
Figure 10:
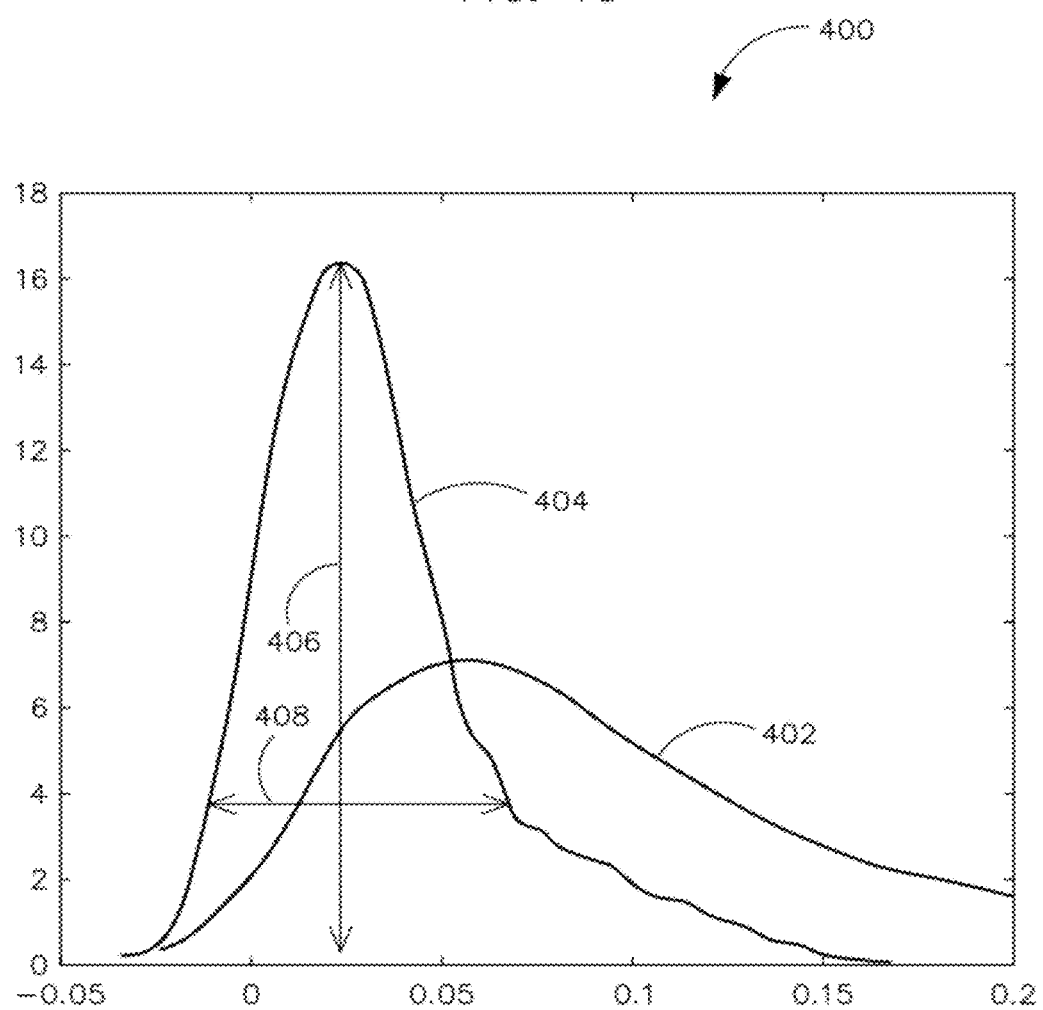
FIG. 10 is a histogram illustrating a height and width of the histogram for evaluation tissue condition according to an embodiment of the invention.

By example, a patient presented with a soft tissue injury can be monitored over time. At selected points, the injured tissue can be visualized through ultrasound and the tissue functionality and mechanical behavior histograms generated. The normalized aspect ratio can be plotted and provide an ongoing ability to monitor the injured tissue. Furthermore, a single patient can be compared to existing patients data for similar injuries and determine if the injury is healing at an expected rate, slow rate, or at an accelerated rate. Referring to FIGS. 8-10, subsequent steps of at least one embodiment of the aspect ratio analysis process are illustrated. Referring to FIG. 8, a mechanical behavior field is illustrated (typically done in color for shown here in black/white) which is a result of the ROI analysis in one of the images that is subsequent to the image of FIG. 5. Referring to FIG. 8, ROI 200 of FIG. 5 has moved from its location in the image (from where it was in FIG. 5) and has clearly distorted in shape as well. Referring to FIG. 9, the tissue functionality fields are obtained using methods known in the art. That is, relationships between elements can be established using known techniques and using measured echoes at the subsequent images.

$$NC_N(\epsilon_N) = A_1\epsilon_1 + A_2\epsilon_2 + \ldots + A_N\epsilon_N$$

In the above equation, tissue functionality $NC(\epsilon)$, measured strains $\epsilon$, and relations are established from frame to frame via the variables A. Tissue functionality $NC(\epsilon)$ and strain $\epsilon$ are measured as a function of time. With the above relation, the time factor can be struck and simple tissue functionality relations may be evaluated. Once the tissue functionality is established, a tissue functionality gradient can be evaluated using the relationship as follows:

$$SG_{\varepsilon_2-\varepsilon_1} = \frac{NC(\varepsilon_2) - NC(\varepsilon_1)}{\varepsilon_2 - \varepsilon_1}$$

As such, the tissue functionality gradient can be calculated and is specific to tissue type or tissue health (and therefore varies over time as a tissue heals, for instance). Thus, tissue functionality fields are calculated and illustrated in FIG. 9. Referring now to FIG. 10, the calculated tissue functionality fields from FIG. 9 can be presented in histogram form 400 having tissue functionality level along the x-axis and number of occurrences as counts in the y-axis. The illustrated curves of FIG. 10 include an injured tissue 402 corresponding to pixel stresses obtained from FIG. 9. However, as the tissue heals over time, the tissue will be illustrated having a more uniform color and lower stress levels. Thus, histogram 404 illustrates a tissue that is significantly healthier than that illustrated in histogram 402. That is, histogram 402 is shallower and wider (having pixels with higher stress) when compared to healthy tissue of histogram 404. Thus, the illustrated histograms provide an objective measure of health that can be simply evaluated by obtaining a ratio of the height 406 of the histogram 404 versus its width 408. Further, the cutoff for determining width 408 can be obtained based on a number of counts (roughly 4 in FIG. 8), but can be any number based on imaging circumstances, pixel size, etc. . . . And, it is to be recognized that the ratio of height 406/width 408 will increase with time as the tissue heals. That is, less pixels will tend to have a high stress level and more will lean toward an increased mean value. The ratio can be ascertained over time, according to the invention, as a means to objectively determine the health of a tissue from dynamic images obtained while flexing the tissue, and over a period of weeks or months.

In another embodiment, there is implementation of automated tendon/ligament identifier: The image texture of tendon/ligament is different from other type of tissues, such as fat, muscle and skin, hence automated tissue "differentiation", also known as "segmentation", may be possible by implementing existing digital image processing/machine vision algorithm.

In another embodiment, tracking of all pixels in view space: Treating whole image as ROI and track all key pixels. Tracking all pixels can be time consuming. However, by splitting the tracking procedure into multiple cores, the calculation speed can be drastically reduced.

Furthermore, the ROI data points, including the neighboring points included within the algorithm, the distance between these points ($\Delta x$, $\Delta y$) be modified. in current code, default pixel distance is set at 10 pixels. However, a user can key in any pixel spacing. Generally, smaller pixel spacing results in a higher analysis resolution. On the other hand, larger pixel spacing results on a lower analysis resolution.

The following scenario provides an example: A patient is properly scanned with any ultrasound system. The dynamic (video) ultrasound images (CINE mode) of gradually deforming tissue are captured. Captured dynamic (video) ultrasound images are sent to PAC (Picture Archive Center) as part of DICOM (Digital Imaging and Communications in Medicine) format patient's information. In image diagnosis, radiologist retrieves patient's DICOM data, selects the ROI (or perhaps first performs one or more FOI determinations) and applies an embodiment of the present invention. Then, a Radiologist more accurately diagnoses pathology with deduced data from supplemental information.

Another example includes: A is patient properly scanned with any ultrasound system. The dynamic (video) ultrasound images (CINE mode) of gradually deforming tissue are captured. B1) Captured dynamic (video) ultrasound images sent to computer connected to ultrasound system. B2) ROI selected and an embodiment of the present invention for ROI tracking is applied on-site in the computer connected to ultrasound system. The deduced results are put into DICOM format patient file and sent to PAC. D) Diagnosis.

In yet another example, the ROI tracking method is employed: A) The patient properly scanned with any ultrasound system. The dynamic (video) ultrasound images (CINE mode) of gradually deforming tissue are captured. In the captured dynamic (video) ultrasound images, the ROIs are selected and analyzed with the ROI tracking methods programmed into ultrasound system. The deduced results are put into DICOM format patient file and sent to PAC. D) Diagnosis.

Currently ROI is selected by applying clicking action on the pixels that defines ROI Alternatively, a user can select ROI by encircling ROI with mouse movement. For example, the pencil feature in Microsoft paint program. Similarly, defining ROI with encircling ROI with tablet pen on touch screen can be an option.

The pixel tracking can be achieved by actually tracking the texture of sub-regions (currently circles) surrounding each target pixel. The size of disk-shaped sub-region can influence the tracking result. Larger sub-regions track better. Currently, the radius of sub-region disk is set at 20 pixels, but this can range significantly depending upon system user's selection. The size of the sub-region can be optimized. A differently shaped sub-region (square or rectangular) may be chosen alternatively.

Some of the major concept elements behind the ROI tracking methods are the evaluation of deformation-dependent tissue functionality named "stiffness gradient" by measuring the echo intensity change within the ROI. Indeed the echo intensity within ROI and sub-region (around target pixel)) change from frame-to-frame. However the magnitude change of echo intensity or texture (intensity of group of pixels) is ASSUMED to be small if TWO consecutive images are compared. Hence, tracking a single pixel can be properly achieved by tracking the sub-region surrounding the target pixel. The process of tracking texture is executed by slightly moving sub-region disk around target pixel and comparing texture in each step. Currently, a mathematically defined norm (summation of echo intensity differences of all pixels within sub-region) is used as the parameter to check how well newly found sub-region matches with original sub-region. If the both sub-regions are a good match, the echo intensity difference between each pixel is zero, hence the norm is zero. A newly found sub-region that output the minimum norm is ASSUMED as the perfect match and the pixel in its center is considered as the new location of target pixel.

If two sub-regions match well, the norm evaluated will be zero. In reality a zero norm can typically not be reached. Therefore a newly found sub-region that output the minimum norm is ASSUMED as a good match and the pixel in its center is considered as the new location of target pixel. Hence setting up a rigor yet achievable the criteria for norm will be important. On the other hand, if a large norm is chosen as the criterion for matching, the matching texture can be found fast yet not rigorous enough. Hence, setting proper norm criterion for terminating sub-region reach will be practical.

Another embodiment includes a feature to present Stiffness Gradient Histogram of fixed size disk-shaped sub-ROI is added. ROI analysis can be completed and Stiffness Gradient color map is presented, user can move cursor to any color coated pixel within the ROI color map to select the target pixel by clicking action. Once the target pixel is selected, a fixed size (this size can be selected by user) disk-shaped sub-ROI will be created around the target pixel for sub-ROI Stiffness Gradient assessment. Multiple ROIs and sub-ROIs can be used to generate a Stiffness Gradient Histogram which can be selected from same analyzed image (case) or different analyzed image (case) for more standardized compare.

The drawback of the ROI Stiffness Gradient Histogram evaluated from user-selected ROI (flexible size and shape) is the size dependency. If ROIs with significantly different size are compared, the deduced Stiffness Gradient Histograms will not be comparable. To solve this drawback, a feature for selecting a fixed size and disk-shaped sub-ROIs and evaluation of sub-ROI histograms are included as an embodiment of the invention.

In addition, following statistical indices are also evaluated from a Stiffness Gradient Histogram and presented on the view window Mean: Mean value of the histogram Variance: Second order moment around mean value that represents the "wideness" of the histogram Skewness: Third order moment around mean value that represents the "measure of the asymmetry" of the histogram Kurtosis: Fourth order moment about mean value that represents the "peakedness" of the histogram Aspect Ratio: Also a parameter shows the "peakedness" of the histogram.

It is to be understood that the invention is not limited in its application to the details of construction and the arrangement of components set forth in the following description or illustrated in the following drawings. The invention is capable of other embodiments and of being practiced or of being carried out in various ways.

The disclosed method utilizes unique tissue (material) properties in a selected ROI and a tracking algorithm and ultrasound echo single/image analysis algorithm to achieve evaluation of tissue type/status specific mechanical functionality.

A technical contribution for the disclosed method and apparatus is that it provides for a computer implemented for ultrasound image processing.

In accordance with still another aspect of the invention, a method for deducing simple image output or numerical scale for monitoring tissue pathology includes feature that evaluates and presents of a local or total tissue stiffness-strain relation with selected and processed ROI (region of interest). Then the stiffness gradient is further evaluated as over-all slope of the deduced tissue stiffness-strain relation. The deduced tissue functionality (stiffness, stiffness-gradient) or tissue mechanical behavior (tissue deformation, displacement, rate of deformation and rate of displacement) at each image pixel can be presented as easy understand color map. The same information can be also presented in the form of histogram plot or probability distribution function plot. Finally, the shape aspect ratio of these plots can be calculated as a numerical single number ordinal scale that represents the tissue health. All these information can be evaluated from the ultrasound images captured from same pathological tissue location of the same patient at different visits. Finally deduced information can be compared and used to monitor heal or progress of tissue pathology.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD- ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

In accordance with one embodiment of the invention, an ultrasound system includes an ultrasound transducer adapted to obtain a dynamic series of echo signals of a subject tissue at different deformation states, and an image processor for generating and displaying ultrasound images of the tissue. The processor is configured to generate dynamic images that correspond to the dynamic series of echo signals, identify a plurality of pixels within a region of interest (ROI) of a first of the generated images, evaluate local tissue mechanical behavior by tracking the displacement, deformation, and echo intensity of the identified plurality of pixels from the first image to subsequent images based on groups of pixels that correspond to each of the identified plurality of pixels, determine tissue functionality in the subject at the tracked pixel locations, and display the tissue functionality in dynamic images that corresponds to the tracked pixel locations.

In accordance with another embodiment of the invention, a method of determining a deformed state of a tissue in ultrasound images, the method includes selecting pixels that are within a region of interest (ROI) of a first ultrasound image of a tissue, wherein the tissue is at a first state of deformation, identifying pixels that surround the selected pixels in the first ultrasound image, evaluating a local tissue mechanical behavior by tracking the selected pixels from the first ultrasound image to subsequent locations in subsequent ultrasound images using the identified pixels that surround the selected pixels, wherein the subsequent ultrasound images correspond to different states of tissue deformation, determining functionality of the tissue at the subsequent locations of the identified pixels, and displaying the functionality at their original or subsequent locations in an image of the tissue.

In accordance with yet another embodiment of the invention, a non-transitory computer readable storage medium having stored thereon a computer program comprising instructions which when executed by a computer cause the computer to obtain a dynamic series of echo signals of a subject taken using an ultrasound transducer with a tissue of the subject at different states of deformation, generate first and second images using the obtained series of echo signals, identify target pixels and their neighboring pixels in the first image, assume locations of the target pixels and their neighboring pixels in the second image, calculate values of a mathematical norm based on the target pixels and their neighboring pixels in the first image and based on their assumed location in the second image, derive actual locations of at least the target pixels in the second image based on the values of the mathematical norm, and overlay deduced functionality or mechanical behavior of the tissue that correspond to their actual locations in the original or second image.

In accordance with still another embodiment of the invention, a method for monitoring tissue pathology includes generating a first tissue functionality histogram/probability density function plot based at least in part upon motion or deformation of a first pixel between a first ultrasound image at a first deformed state and a second ultrasound image at a second deformed state, calculating a first ordinal scale aspect ratio based upon the first tissue functionality histogram, generating a second tissue functionality histogram/probability density function plot based at least in part upon motion of a second pixel between a third ultrasound image at a third deformed state and a fourth ultrasound image at a fourth deformed state, calculating a second ordinal scale aspect ratio based upon the second tissue functionality histogram/probability density function plot, and generating a time series plot based on the first ordinal scale aspect ratio and the second ordinal scale aspect ratio as an indicator of a tissue pathology.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An ultrasound system comprising:
   an ultrasound transducer adapted to obtain a dynamic series of echo signals of a subject tissue at different deformation states; and
   an image processor for generating and displaying ultrasound images of the subject tissue, the image processor configured to:
     generate dynamic images that correspond to the dynamic series of echo signals;
     identify a plurality of pixels representing the subject tissue within a region of interest (ROI) of a first of the generated images;
     evaluate local tissue mechanical behavior by tracking the displacement, deformation, and echo intensity of the identified plurality of pixels from the first image to subsequent images based on groups of pixels neighboring each of the identified plurality of pixels;
     determine tissue functionality in the subject tissue at the tracked pixel locations;
     display the tissue functionality in dynamic images that correspond to the tracked pixel locations;
     generate a histogram or probability density function plot of the multiple tissue functionality parameters that can be deduced from determined stiffness-strain relationship;
     generate an ordinal scale from an aspect ratio of the histogram or probability density function plot; and
     compare the ordinal scale to a previous ordinal scale in order to determine an amount of healing in a tissue that has occurred since imaging data used to generate the previous ordinal scale was obtained;
   wherein the local tissue mechanical behavior comprises one of displacement and deformation of the identified plurality of pixels; and
   wherein the tissue functionality comprises a stiffness-strain relationship and other parameters deduced from this relation.

2. The ultrasound system of claim 1 wherein the image processor is configured to generate a color map of the subject tissue having a color that corresponds to the tissue functionality parameters that can be deduced from a determined stiffness-strain relation.

3. The ultrasound system of claim 1 wherein the image processor is configured to evaluate local tissue mechanical behavior of the identified plurality of pixels by being configured to:
   a) assume an initial displacement an identified pixel of the identified plurality of pixels and a deformation of the neighbor-region of the identified pixel from the first image to one of the subsequent images;
   b) calculate a value of a mathematical function based on a pixel location of the identified pixel in the first image and an assumed location of the identified pixel in the subsequent image and using its corresponding group of pixels;
   c) compare the value of the mathematical function to a termination value, and:
      if the value is above the termination value, then the image processor is configured to:
         iterate by being configured to perturb the assumed initial displacement of the identified pixel and the deformation of the neighbor-region of the identified pixel; and
         return to step b);
      if the value is below the termination value, then the image processor is configured to:
         determine the displacement of the identified pixel and the deformation of the neighbor-region of the identified pixel based on the value; and
         terminate the iteration.

4. The ultrasound system of claim 1 wherein the image processor is configured to:
   select a fiber of interest (FOI) within one of the dynamic images;
   determine whether the FOI shows a clear deformation in subsequent dynamic images;
   identify the FOI as a candidate for selection of the ROI based on the determination that the FOI has clearly presented the deformation.

5. The ultrasound system of claim 1 wherein:
   the image processor is comprised of multiple computer cores, each core comprising a central processing unit (CPU); and
   wherein the image processor is configured to evaluate the local tissue mechanical behavior by:
      tracking one of the identified plurality of pixels from the first image to the subsequent images using one of the multiple computer cores; and
      tracking another of the identified plurality of pixels from the first image to the subsequent images using another of the multiple computer cores.

6. An ultrasound system comprising:
   an ultrasound transducer adapted to obtain a dynamic series of echo signals of a subject tissue at different deformation states; and
   an image processor for generating and displaying ultrasound images of the subject tissue, the image processor configured to:
      generate dynamic images that correspond to the dynamic series of echo signals;
      identify a plurality of pixels representing the subject tissue within a region of interest (ROI) of a first of the generated images;
      evaluate local tissue mechanical behavior by tracking the displacement, deformation, and echo intensity of the identified plurality of pixels from the first image to subsequent images based on groups of pixels located within a neighbor-region of each of the identified plurality of pixels;
      determine tissue functionality in the subject tissue at the tracked pixel locations; and
      display the tissue functionality in dynamic images that correspond to the tracked pixel locations; and
   wherein the image processor is configured to evaluate local tissue mechanical behavior of the identified plurality of pixels by being configured to:
      a) assume an initial displacement of an identified pixel of the identified plurality of pixels and a deformation of the neighbor-region of the identified pixel from the first image to one of the subsequent images;
      b) calculate a value of a mathematical function based on a pixel location of the identified pixel in the first image and an assumed location of the identified pixel in the subsequent image and using its corresponding group of pixels;
      c) compare the value of the mathematical function to a termination value, and:
         if the value is above the termination value, then the image processor is configured to:
            iterate by being configured to perturb the assumed initial displacement of the identified pixel and the deformation of the neighbor-region of the identified pixel; and
            return to step b);
         if the value is below the termination value, then the image processor is configured to:
            determine the displacement of the identified pixel and the deformation of the neighbor-region of the identified pixel based on the value; and
            terminate the iteration.

7. An ultrasound system comprising:
   an ultrasound transducer adapted to obtain a dynamic series of echo signals of a subject tissue at different deformation states; and
   an image processor for generating and displaying ultrasound images of the subject tissue, the image processor configured to:
      generate dynamic images that correspond to the dynamic series of echo signals;
      identify a plurality of pixels representing the subject tissue within a region of interest (ROI) of a first of the generated images;
      evaluate local tissue mechanical behavior by tracking the displacement, deformation, and echo intensity of the identified plurality of pixels from the first image to subsequent images based on groups of pixels neighboring each of the identified plurality of pixels;
      determine tissue functionality in the subject tissue at the tracked pixel locations;
      display the tissue functionality in dynamic images that correspond to the tracked pixel locations;
      select a fiber of interest (FOI) within one of the dynamic images;
      determine whether the FOI shows a deformation in subsequent dynamic images; and
      identify the FOI as a candidate for selection of the ROI based on the determination that the FOI has shown the deformation.

8. An ultrasound system comprising:
   an ultrasound transducer adapted to obtain a dynamic series of echo signals of a subject tissue at different deformation states; and an image processor for generating and displaying ultrasound images of the subject tissue, the image processor configured to:
  generate dynamic images that correspond to the dynamic series of echo signals;
  identify a plurality of pixels representing the subject tissue within a region of interest (ROI) of a first of the generated images;
  evaluate local tissue mechanical behavior by tracking the displacement, deformation, and echo intensity of the identified plurality of pixels from the first image to subsequent images based on groups of pixels neighboring each of the identified plurality of pixels;
  determine tissue functionality in the subject tissue at the tracked pixel locations; and
  display the tissue functionality in dynamic images that correspond to the tracked pixel locations;
wherein the image processor is comprised of multiple computer cores, each core comprising a central processing unit (CPU); and
wherein the image processor is configured to evaluate the local tissue mechanical behavior by:
  tracking one of the identified plurality of pixels from the first image to the subsequent images using one of the multiple computer cores; and
  tracking another of the identified plurality of pixels from the first image to the subsequent images using another of the multiple computer cores.

* * * * *

UNITED STATES PATENT AND TRADEMARK OFFICE
CERTIFICATE OF CORRECTION

PATENT NO. : 8,840,555 B2  
APPLICATION NO. : 13/293499  
DATED : September 23, 2014  
INVENTOR(S) : Miller et al.

Page 1 of 1

It is certified that error appears in the above-identified patent and that said Letters Patent is hereby corrected as shown below:

In The Specification

Col. 10, line 5, delete "$C_N(\epsilon_N) = a_1 \epsilon_N + a_2 \epsilon_{N-1} + \ldots + a_m \epsilon_{N+m-1}$" and substitute therefore -- $C_N(\varepsilon_N) = a_1 \varepsilon_N + a_2 \varepsilon_{N-1} + \cdots + a_m \varepsilon_{N+m-1}$ --; and Col. 10, line 8, delete "$C_N(\epsilon_N)$" and substitute therefore -- $C_N(\varepsilon_N)$ --.

Col. 11, line 47, delete "$NC_N(\epsilon_N) = A_1 \epsilon_1 + A_2 \epsilon_2 + \ldots + A_N \epsilon_N$" and substitute therefore -- $NC_N(\varepsilon_N) = A_1 \varepsilon_1 + A_2 \varepsilon_2 + \cdots + A_N \varepsilon_N$ --; and Col. 11, line 49, delete "NC($\epsilon$)," and substitute therefore -- NC($\varepsilon$), --; and Col. 11, line 50, delete "strains $\epsilon$," and substitute therefore -- strains $\varepsilon$, --; and Col. 11, line 51, delete "NC($\epsilon$)" and substitute therefore -- NC($\varepsilon$) --; and Col. 11, line 52, "strain $\epsilon$" and substitute therefore -- strain $\varepsilon$ --.

Col. 12, line 38, delete "modified. in" and substitute therefore -- modified. In --.

Col. 13, line 25, delete "pixel))" and substitute therefore -- pixel) --.

Col. 14, line 9, delete "histogram" and substitute therefore -- histogram. --.

Signed and Sealed this  
Seventeenth Day of February, 2015

Michelle K. Lee  
*Deputy Director of the United States Patent and Trademark Office*